United States Patent
Cho et al.

(10) Patent No.: US 12,012,454 B2
(45) Date of Patent: Jun. 18, 2024

(54) ANTI-TUMOR ANTIGEN NANOBODY AND NUCLEIC ACID ENCODING SEQUENCE THEREOF, AND USES OF THE SAME

(71) Applicant: China Medical University Hospital, Taichung (TW)

(72) Inventors: Der-Yang Cho, Taichung (TW); Shao-Chih Chiu, Taichung (TW); Shi-Wei Huang, Taichung (TW); Chih-Ming Pan, Taichung (TW); Mei-Chih Chen, Taichung (TW); Yu-Chuan Lin, Taichung (TW); Yeh Chen, Taichung (TW)

(73) Assignee: CHINA MEDICAL UNIVERSITY HOSPITAL, Taichung (TW)

( * ) Notice: Subject to any disclaimer, the term of this patent is extended or adjusted under 35 U.S.C. 154(b) by 0 days.

(21) Appl. No.: 17/692,599

(22) Filed: Mar. 11, 2022

(65) Prior Publication Data

US 2022/0306747 A1    Sep. 29, 2022

Related U.S. Application Data

(60) Provisional application No. 63/165,266, filed on Mar. 24, 2021.

(51) Int. Cl.
*C07K 16/28* (2006.01)
*A61P 35/00* (2006.01)

(52) U.S. Cl.
CPC .......... *C07K 16/2833* (2013.01); *A61P 35/00* (2018.01); *C07K 2317/31* (2013.01); *C07K 2317/52* (2013.01); *C07K 2317/565* (2013.01); *C07K 2317/569* (2013.01); *C07K 2317/76* (2013.01)

(58) Field of Classification Search
CPC ............ C07K 16/2833; C07K 2317/31; C07K 2317/52; C07K 2317/565; C07K 2317/569; C07K 2317/76; A61P 35/00
See application file for complete search history.

(56) References Cited

FOREIGN PATENT DOCUMENTS

TW           202035456       10/2020
WO     WO-2011051327 A2 *   5/2011  ............. C07K 16/00

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*
Kussie, Paul H., "A Single Engineered Amino Acid Substitution Changes Antibody Fine Specificity", 1994, Journal of Immunology 152(1): pp. 146-152. (Year: 1994).*

(Continued)

*Primary Examiner* — Aurora M Fontainhas
*Assistant Examiner* — Selam Berhane
(74) *Attorney, Agent, or Firm* — WPAT, P.C

(57) ABSTRACT

The present disclosure provides an anti-tumor antigen nanobody that specifically binds to a human leukocyte antigen-G. The present disclosure also provides the nucleic acid sequence of the anti-tumor antigen nanobody, use of the anti-tumor antigen nanobody for treating cancer and immune-related disorders, and a method for detecting expression levels of HLA-G.

17 Claims, 14 Drawing Sheets
(3 of 14 Drawing Sheet(s) Filed in Color)
Specification includes a Sequence Listing.

(56) References Cited

OTHER PUBLICATIONS

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

* cited by examiner

ANTI-TUMOR ANTIGEN NANOBODY AND NUCLEIC ACID ENCODING SEQUENCE THEREOF, AND USES OF THE SAME

CROSS-REFERENCE TO RELATED APPLICATION

This application claims priority of Provisional Application No. 63/165,266, filed on Mar. 24, 2021, the content of which is incorporated herein in its entirety by reference.

BACKGROUND OF THE INVENTION

1. Field of the Invention

The present invention relates to an anti-tumor antigen nanobody and nucleic acid encoding sequences thereof, and uses of the same.

2. The Prior Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for consecutive years.

Conventional cancer treatments include surgery, radiation therapy, chemotherapy, and target therapy. Cancer immunotherapy is another method for treating cancer except the above methods. The immune system of the patient is activated in the cancer immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors. However, the current tumor treatments still have the problems of ineffectiveness and strong side effects, and even lead to other immune-related disorders.

Human leukocyte antigen-G (HLA-G) has been found to be highly expressed on a variety of solid tumors, and has the property of suppressing immune cells. Therefore, researchers have been committed to developing HLA-G as target molecules for tumor identification and to find out whether these target molecules have the potential to become anti-cancer drugs.

In order to solve the above-mentioned problems, those skilled in the art urgently need to develop a novel and effective medicament for treating cancer and immune-related disorders for the benefit of a large group of people in need thereof.

SUMMARY OF THE INVENTION

A primary objective of the present invention is to provide an anti-tumor antigen nanobody that specifically binds to a human leukocyte antigen-G (HLA-G), comprising an amino acid sequence selected from the group consisting of: SEQ ID NO:1, SEQ ID NO:2, SEQ ID NO:3, and any combination thereof.

According to an embodiment of the present invention, the amino acid sequence is an amino acid sequence of a heavy chain variable domain (VHH) of the anti-tumor antigen nanobody.

According to an embodiment of the present invention, the anti-tumor antigen nanobody is conjugated with a fragment crystallizable region (Fc region).

According to an embodiment of the present invention, the anti-tumor antigen nanobody is conjugated with a second antibody to form a bispecific T-cell engager (BiTE), triple specific T-cell engager (TriTE), bispecific killer cell enager (BiKE), triple specific killer cell engager (TriKE), or any bispecific antibody.

According to an embodiment of the present invention, the anti-tumor antigen nanobody blocks interaction and/or binding of the HLA-G with a receptor of the HLA-G.

According to an embodiment of the present invention, the receptor is killer cell immunoglobulin like receptor, two Ig domains and long cytoplasmic tail 4 (KIR2DL4) or leukocyte immunoglobulin-like receptor subfamily B member 1 (LILRB1).

Another objective of the present invention is to provide an isolated nucleic acid encoding the above mentioned anti-tumor antigen nanobody, wherein the isolated nucleic acid comprises a nucleotide sequence selected from the group consisting of: SEQ ID NO:4, SEQ ID NO:5, SEQ ID NO:6, and any combination thereof.

Another objective of the present invention is to provide a pharmaceutical composition, comprising the above mentioned anti-tumor antigen nanobody and a pharmaceutically acceptable carrier.

Another objective of the present invention is to provide a method for treating cancer and immune-related disorders, comprising administering to a subject in need thereof the above mentioned pharmaceutical composition.

Another objective of the present invention is to provide a method for detecting expression levels of HLA-G, comprising administering to a biological sample the above mentioned anti-tumor antigen nanobody.

According to an embodiment of the present invention, the biological sample is blood, urine, sputum, saliva, body fluid or human placenta.

In summary, the anti-tumor antigen nanobody of the present invention has the following effect. The anti-HLA-G nanobody blocks the interaction between HLA-G and one of its receptor killer cell immunoglobulin like receptor, two Ig domains and long cytoplasmic tail 4 (KIR2DL4) and leukocyte immunoglobulin-like receptor subfamily B member 1 (LILRB1) within the 50% blocking activity as IC50 by competitive enzyme linked immunosorbent assay (ELISA), enhances cytolysis and cytotoxicity of human breast cancer cell line MDA-MB-231 with natural killer cells (NK cells), could recognize HLA-G protein from cellular lysate of human cancer cell line MDA-MB-231 and A549 cells by Western blotting analysis, and is used for flow cytometric analysis. The anti-HLA-G nanobody also could recognize HLA-G protein on cell membrane, the expression of HLA-G is co-localized with the plasma membrane marker pan-cadherin on MDA-MB-231 and A549 cells by immunocytochemistry, and is used to detect the expression of HLA-G by immunohistochemistry (IHC) staining, thereby achieving the effect of treating cancer and immune-related disorders. In particular, compared with the conventional antibodies, which have the disadvantages of low yield and poor effect, the gene must be transfected into cells by a vector to express the antibody function, the anti-tumor antigen nanobody of the present invention can be prepared in vitro on a large scale, and directly administered to the individual in need for treatment. In addition, the present invention can also achieve the effect of detecting the expression level of HLA-G.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1A:
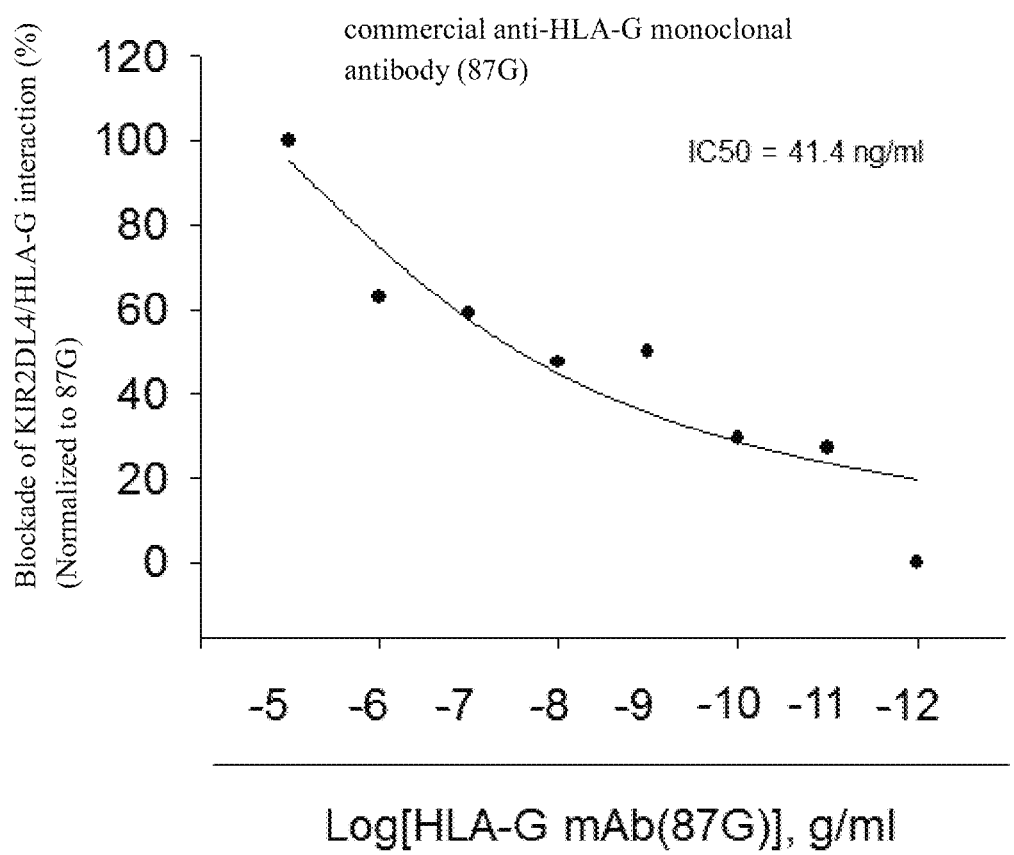
FIGS. 1A-1H show that the HLA-G/killer cell immunoglobulin like receptor, two Ig domains and long cytoplasmic tail 4 (KIR2DL4) or leukocyte immunoglobulin-like receptor subfamily B member 1 (LILRB1) axis blockade of the anti-HLA-G nanobodies are determined by competitive enzyme linked immunosorbent assay (ELISA), wherein LILRB1 represents leukocyte immunoglobulin-like receptor subfamily B member 1; KIR2DL4 represents killer cell immunoglobulin like receptor, two Ig domains and long cytoplasmic tail 4; nb represents nanobody; 87G represents commercial anti-HLA-G monoclonal antibody.
Figure 1B:
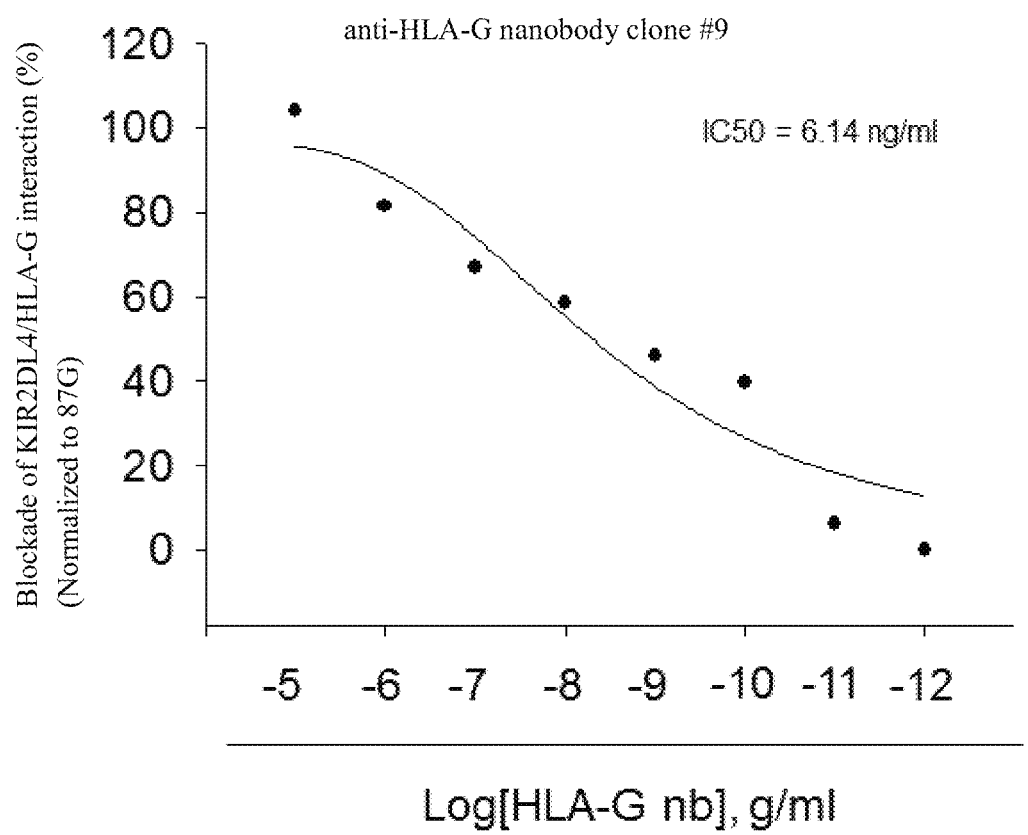
Figure 1C:
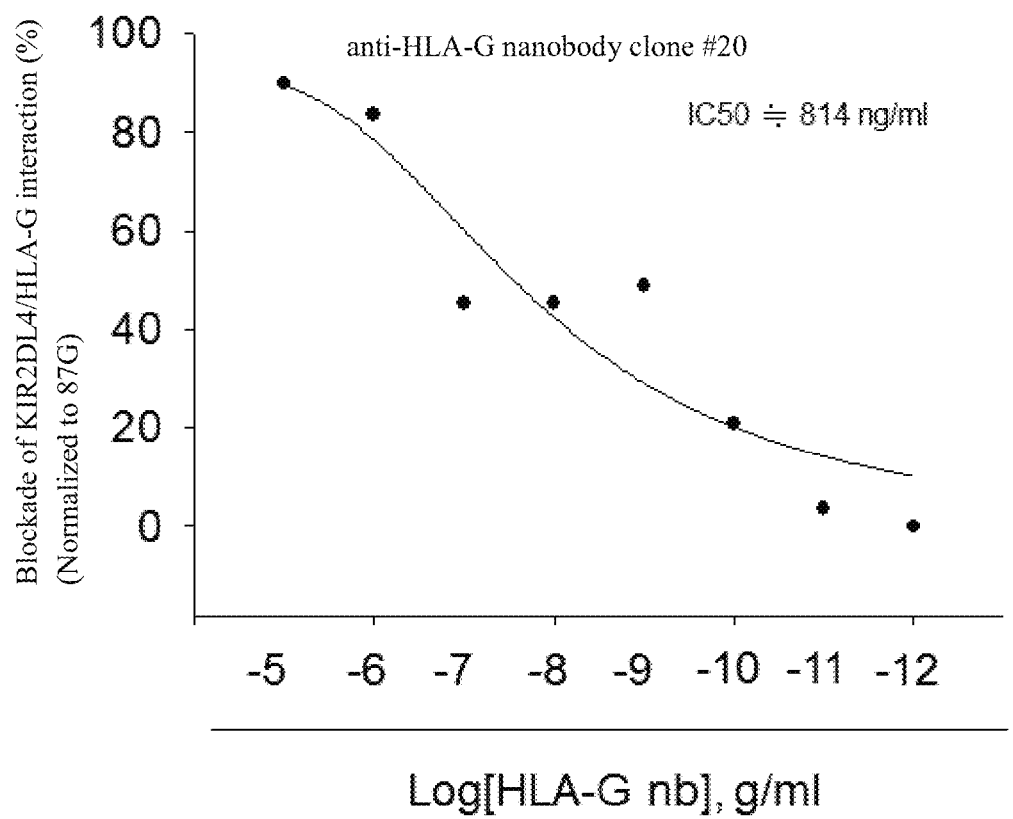
Figure 1D:
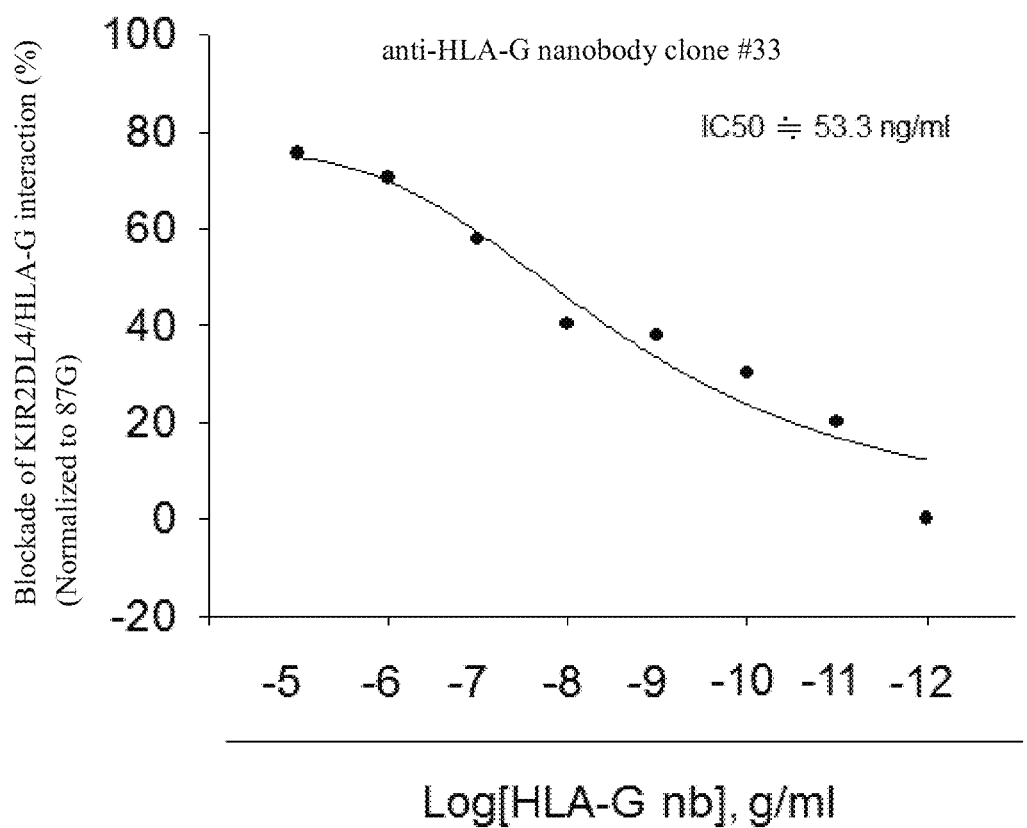
Figure 1E:
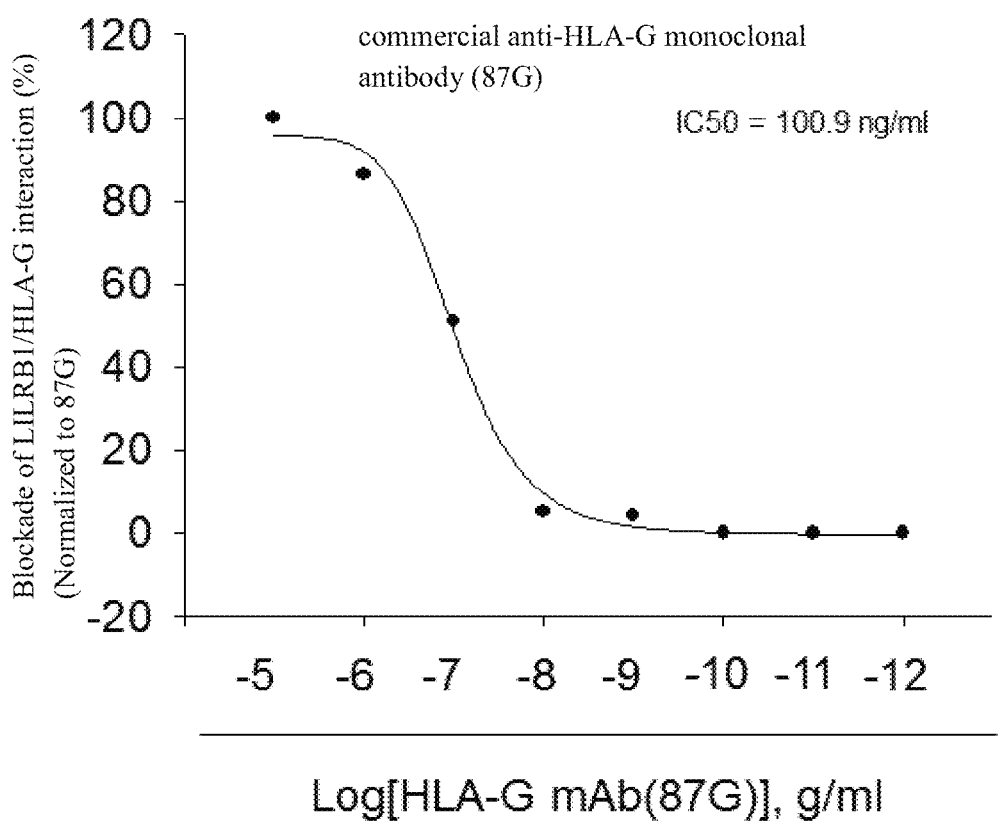
Figure 1F:
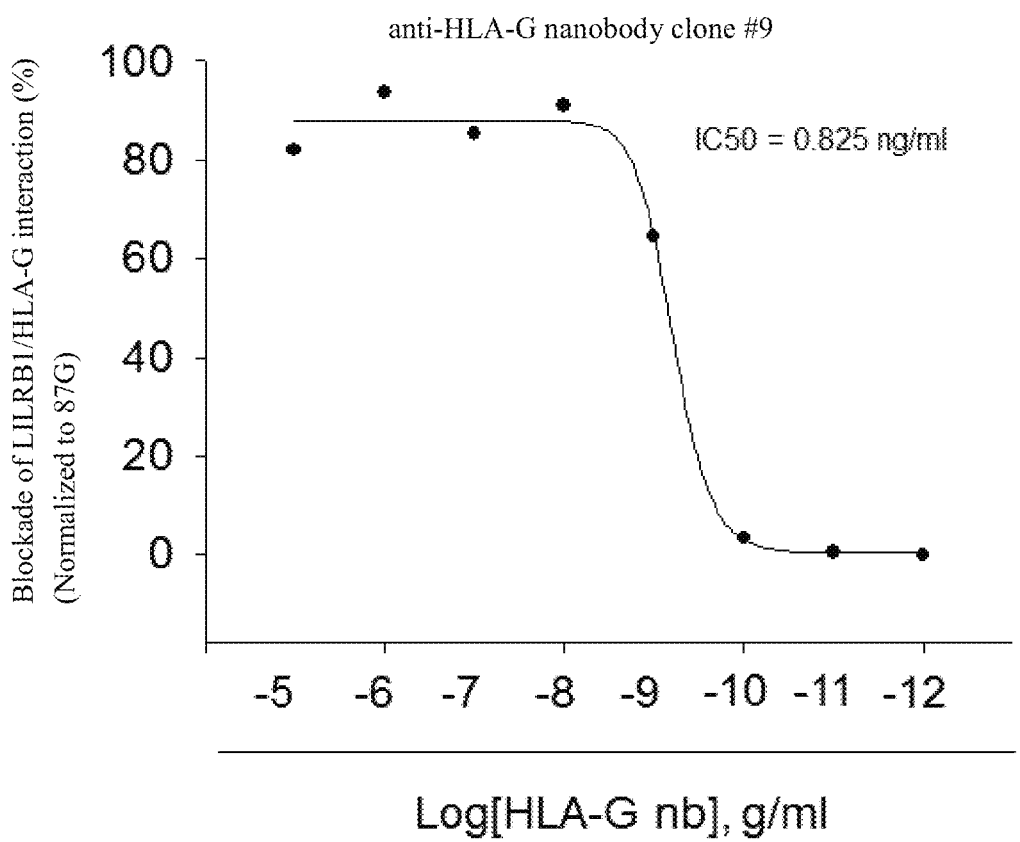
Figure 1G:
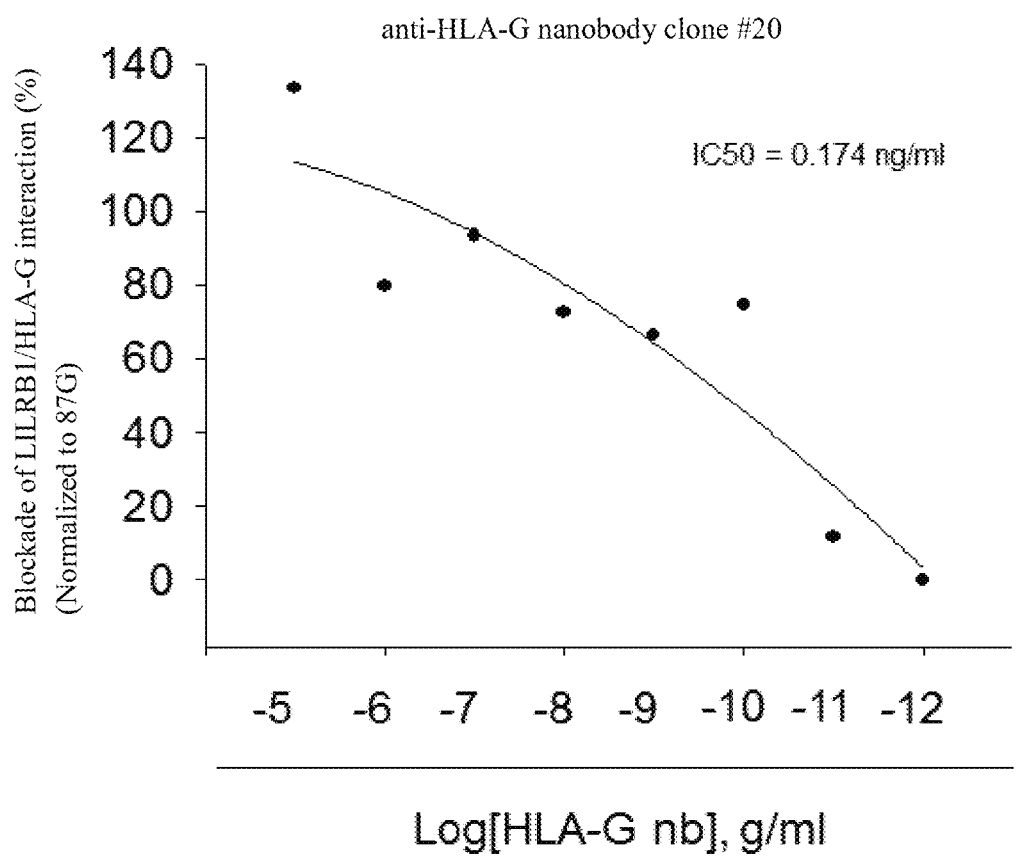
Figure 1H:
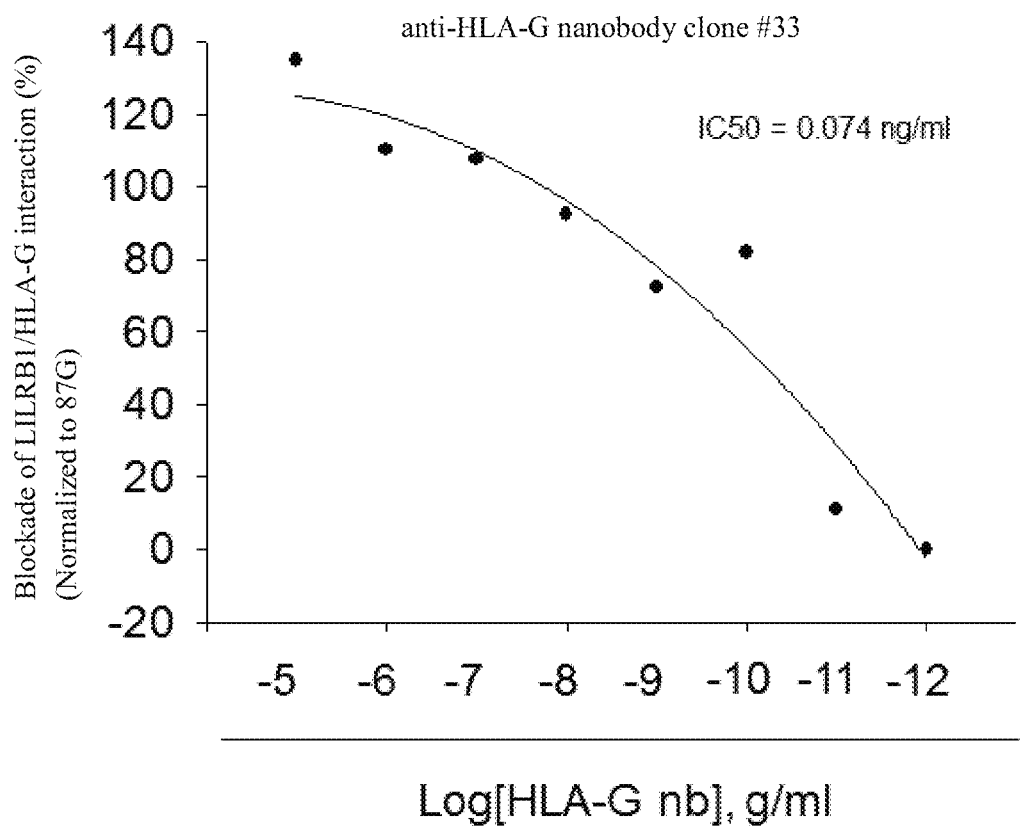

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the terms "anti-human leukocyte antigen-G (HLA-G) nanobody (NB)" and "anti-tumor antigen nanobody" can be used interchangeably.

As used herein, the term "second antibody" refers to the antibody conjugated with the nanobody to form a bispecific T-cell engager (BiTE), triple specific T-cell engager (TriTE), bispecific killer cell enager (BiKE), triple specific killer cell engager (TriKE), or any bispecific antibody. Preferably, the second antibody includes, but is not limited to, anti-CD3ε antibody, anti-programmed cell death ligand 1 (PD-L1) antibody, anti-programmed cell death ligand 2 (PD-L2) antibody, anti-T-cell immunoglobulin domain and mucin domain 3 (Tim3) antibody, anti-epidermal growth factor receptor (EGFR) antibody, anti-EGFRvIII antibody, anti-human epidermal growth factor receptor 2 (Her2) antibody, anti-B-cell maturation antigen (BCMA) antibody, anti-CD19 antibody, anti-CD20 antibody, anti-CD34 antibody, anti-CD16 antibody, Fc, anti-epithelial cell adhesion molecule (EpCAM) antibody, anti-mesothelin antibody, anti-New York esophageal squamous cell carcinoma-1 (NY-ESO-1) antibody, anti-glycoprotein 100 (gp100) antibody, and anti-Muc 1 antibody.

As used herein, the term "treating" or "treatment" refers to alleviating, reducing, ameliorating, relieving or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, and intralesional injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

As used herein, the term "nucleic acid", "nucleic acid sequence" or "nucleic acid fragment" refers to a sequence of deoxyribonucleotides or ribonucleotides in single- or double-stranded forms, and comprises known naturally occurring nucleotides or artificially chemical mimics. As used herein, the term "nucleic acid" is used interchangeably with the terms "gene", "cDNA", "mRNA", "oligonucleotide" and "polynucleotide".

Example 1

Preparation of Anti-HLA-G Nanobody

In this example, the preparation process of the anti-human leukocyte antigen-G (HLA-G) nanobody (NB) is as follows. The heavy chain variable domain (VHH) production protocol is as follows. The VHH gene was constructed in expression vector pET22b (Amp resistance) or pSB-init (CmR resistance); The plasmid was identified by restriction enzyme digestion and sequenced verification. 1 µL identified plasmid (about 50 ng) was added to BL21(DE3), and incubated overnight at 37° C. LB culture medium containing resistance was inoculated with a single colony and the cultures were incubated overnight at 37° C., 220 r/min Overnight culture was inoculated in a fresh LB medium (10 L-20 L) containing resistance at a ratio of 1:100, and cultured at 37° C. and 220 r/min. It was cooled to room temperature when the $OD_{600}$ reaches 0.8. Isopropyl-β-D-thiogalactopyranoside (IPTG) was added with a final concentration of 0.1 mM and induced overnight at 20° C., 220 r/min. The cells and supernatant were harvested after cell disruption by centrifugation (20 mM Tris pH 8.0, 150 mM NaCl). Supernatant was combined with Ni-NTA beads (1 mL) by flow-through. The Ni-NTA beads were washed and eluted with buffers containing suitable gradient imidazole (10 mM, 20 mM, 50 mM, 100 mM, 250 mM and 500 mM). Elution fraction was analyzed by SDS-PAGE, and the subsequent purification scheme was determined according to the purity and yield of the protein (ion exchange chromatography or gel filtration chromatography). The protein that meets the requirements was separated and purified by gel filtration chromatography, and buffer was replaced with PBS buffer. The protein component was analyzed by SDS-PAGE, the components were merged and concentrated that meet the requirements, filtered with 0.22 µm filter and aliquot. The protein was stored at −20° C. or lower.

The production and purification of nanobodies are from *E. coli*. For producing nanobody form *E. coli* is modified in view of Microb Cell Fact. 2019 Mar. 11; 18(1):47. In brief, the *E. coli* strain HB2151 was used. The plasmid pET (Creative Biolab) coding an ampicillin resistance was used for cytoplasmic protein production. Freshly transformed *E. coli* HB2151 with pET-HLA-G or HLA-G multispecific nanobody plasmids would be inoculated in 5 mL of media containing 50 µg/mL of ampicillin and cultivated at 37° C. for overnight. After that, 1 mL of this pre-culture was inoculated into 100 mL medium and grown at 37° C. After overnight cultivation, two EnPresso booster tablets and an additional dose of the glucose releasing enzyme (0.6 U/L) would be added to each 100 mL culture. At the same time, recombinant nanobody protein expression would be induced by the addition of 1 mM IPTG continued as for 24 hours. Then the cultures would be collected and chilled on ice for 5 min and centrifuged for 15 min at 6,000×g and 4° C. After removal of the supernatant, the cell pellets would be purified by high-capacity Myc-tag binding resin using immobilized metal affinity chromatography (IMAC). The gravity-flow-based chromatography would be carried out under native conditions according to the manufacturer protocol (Clontech Laboratories). Efficient cell lysis would be achieved by addition of 1 mL xTractor cell lysis buffer (Clontech Laboratories) supplemented with EDTA-free protease inhibitor cocktail (Roche Diagnostics) and 25 U endonuclease (Thermo Scientific Pierce) to each 200 mg bacterial cell pellet. After incubation on ice for 15 min and centrifugation at 10,000×g and 4° C. for 20 min for removal of cellular debris, the clarified supernatant would be loaded onto a gravity-flow column containing 1 mL of prepacked resin and incubated at room temperature for 30 min. Before elution of the nanobodies by addition of elution buffer containing 300 mM imidazole, the column would be washed twice with increasing imidazole concentrations of 20 and 40 mM. Removal of imidazole and buffer exchange would be achieved by dialysis against PBS using a cellulose ester membrane with a molecular weight cut-off of 3.5-5 kDa (Spectrum® Laboratories).

The alignment and amino acid sequences of the complementarity determining regions (CDRs) for each clone of anti-HLA-G nanobodies are shown in Table 1. The amino acid sequence of anti-HLA-G nanobody clone #9 is SEQ ID NO:1; The amino acid sequence of anti-HLA-G nanobody clone #20 is SEQ ID NO:2; The amino acid sequence of anti-HLA-G nanobody clone #33 is SEQ ID NO:3; The nucleotide sequence encoding the amino acid sequence of anti-HLA-G nanobody clone #9 is SEQ ID NO:4; The nucleotide sequence encoding the amino acid sequence of anti-HLA-G nanobody clone #20 is SEQ ID NO:5; The nucleotide sequence encoding the amino acid sequence of anti-HLA-G nanobody clone #33 is SEQ ID NO:6.

TABLE 1

| Clone | CDR1 | CDR2 | CDR3 |
|---|---|---|---|
| #9 | GRTYSSNC (SEQ ID NO: 7) | IYTGGDGI (SEQ ID NO: 8) | AADPNRRRMGVGGSC (SEQ ID NO: 9) |
| #20 | GFTVDDSD (SEQ ID NO: 10) | ITSGGGK (SEQ ID NO: 11) | VAPAWTGYGCT (SEQ ID NO: 12) |
| #33 | AYTFSASG (SEQ ID NO: 13) | AATYTRSAKT (SEQ ID NO: 14) | AVARCAGRPDRSTL TSFAW (SEQ ID NO: 15) |

Example 2

HLA-G/Killer Cell Immunoglobulin Like Receptor, Two Ig Domains and Long Cytoplasmic Tail 4 (KIR2DL4) or Leukocyte Immunoglobulin-Like Receptor Subfamily B Member 1 (LILRB1) Axis Blockade of Anti-HLA-G Nanobodies are Determined by Competitive Enzyme Linked Immunosorbent Assay (ELISA)

In this example, the HLA-G/KIR2DL4 axis blockade of the anti-HLA-G nanobodies were determined by competitive ELISA. The procedure is as follows. HLA-G recombinant protein (CAT #: TP305216, Origene) (0.2 mg/ml, 100 µl each well) was coated on 96-well plate overnight at 4° C. Next day, the coating buffer was discarded, and blocked with 3% skin milk for 2 hr at room temperature, followed by washing 5 times with PBST (0.05% Tween in PBS). Different concentrations of anti-HLA-G nanobody (clone #9, #20 or #33) or commercial anti-HLA-G monoclonal antibody (87G) were added overnight at 4° C. After 5 times of washing, biotinylated KIR2DL4 (Sino Biological, Cat: 13052-H02S) (0.2 mg/ml, 100 µl each well) was added for 2 hr at room temperature. After 9 times of washing, each well was incubated with 100 µl PBST containing streptavidin-HRP conjugates (ThermoFisher, Cat No: N100, dilution titer: 5000:1) for 2 hr at room temperature. After 9 times of washing with PBST, 50 µl of TMB substrate for detecting HRP activity (ThermoFisher, Cat No:N301) was added. The reactions were stopped by adding 50 µl stop solution (ThermoFisher, Cat No:N600), and it was measured by ELISA reader using 450 nm channel. The highest concentration of commercial HLA-G monoclonal antibody (87G) was set to 100% blockade of KIR2DL4/HLA-G interaction for calculating other reactions.

In addition, the HLA-G/LILRB1 axis blockade of the anti-HLA-G nanobodies were also determined by competitive ELISA. The procedure is basically the same as above, the differences are: biotinylated KIR2DL4 was replaced with biotinylated LILRB1 (Sino Biological, Cat: 16014-H08H), and the highest concentration of commercial HLA-G monoclonal antibody (87G) was set to 100% blockade of LILRB1/HLA-G interaction for calculating other reactions.

The results of this example are shown in FIGS. 1A-1H, wherein LILRB1 represents leukocyte immunoglobulin-like receptor subfamily B member 1; KIR2DL4 represents killer cell immunoglobulin like receptor, two Ig domains and long cytoplasmic tail 4; nb represents nanobody; 87G represents commercial anti-HLA-G monoclonal antibody. The result of this example demonstrates that commercial anti-HLA-G monoclonal antibody (87G) blocks the interaction between HLA-G and one of its receptor KIR2DL4 within the 50% blocking activity as 41.4 ng/ml (IC50). The anti-HLA-G nanobody clone #9 blocks the interaction between HLA-G and one of its receptor KIR2DL4 within the 50% blocking activity as 6.14 ng/ml (IC50), the blocking activity was normalized to 87G. The anti-HLA-G nanobody clone #20 blocks the interaction between HLA-G and one of its receptor KIR2DL4 within the 50% blocking activity as 814 ng/ml (IC50), the blocking activity was normalized to 87G. The anti-HLA-G nanobody clone #33 blocks the interaction between HLA-G and one of its receptor KIR2DL4 within the 50% blocking activity as 53.3 ng/ml (IC50), the blocking activity was normalized to 87G. Commercial anti-HLA-G monoclonal antibody (87G) blocks the interaction between HLA-G and its another one receptor LILRB1 within the 50% blocking activity as 100.9 ng/ml (IC50). The anti-HLA-G nanobody clone #9 blocks the interaction between HLA-G and its another one receptor LILRB1 within the 50% blocking activity as 0.825 ng/ml (IC50), the blocking activity was normalized to 87G. The anti-HLA-G nanobody clone #20 blocks the interaction between HLA-G and its another one receptor LILRB1 within the 50% blocking activity as 0.174 ng/ml (IC50), the blocking activity was normalized to 87G. The anti-HLA-G nanobody clone #33 blocks the interaction between HLA-G and its another one receptor LILRB1 within the 50% blocking activity as 0.074 ng/ml (IC50), the blocking activity was normalized to 87G.

Example 3

Evaluation of Effect of Anti-HLA-G Nanobody on Enhancing Cytolysis of Human Breast Cancer Cell Line MDA-MB-231 with Natural Killer Cells (NK Cells)

In this example, effect of anti-HLA-G nanobody on enhancing cytolysis of human breast cancer cell line MDA-MB-231 (purchased from American Type Culture Collection (ATCC)) with natural killer cells (NK cells) is evaluated. The procedure is as follows. $1 \times 10^5$ of MDA-MB-231 cells were plating on 12-well plate overnight. Next day, the $5 \times 10^5$ of primary NK cells were added into the wells containing MDA-MB-231 cells. 1 mg/ml of anti-HLA-G nanobody (clone #9, #20 or #33) or 10 µg/ml commercial HLA-G monoclonal antibody (87G, ThermoFisher, Cat No: 14-9957-82) were added. After 48 hr, the specific lysis to MDA-MB-231 cells by primary NK cells were determined by LIVE/DEAD cell-mediated cytotoxicity assay using flow cytometry analysis.

Figure 2:
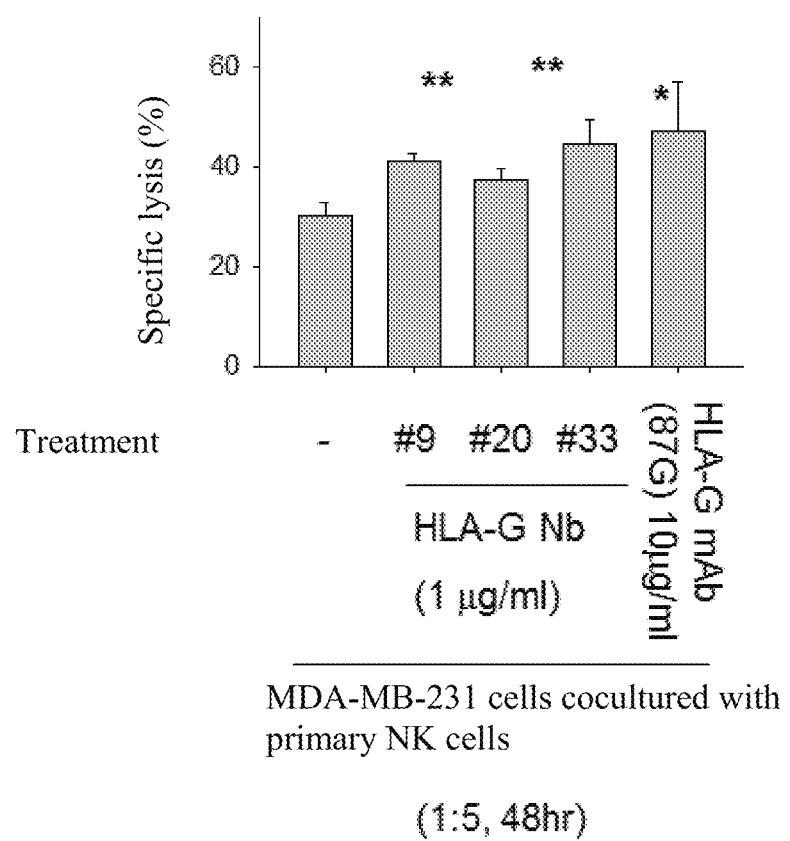
FIG. 2 is a data diagram, showing that the anti-HLA-G nanobody enhances cytolysis of human breast cancer cell line MDA-MB-231 with natural killer cells (NK cells), wherein HLA-G mAB (87G) represents commercial anti-HLA-G monoclonal antibody (87G).

The result of anti-HLA-G nanobody on enhancing cytolysis of human breast cancer cell line MDA-MB-231 with NK cells is shown in FIG. 2. The result of this example demonstrates that anti-HLA-G nanobody clones #9, #20 and #33 enhance NK-induced cytotoxicity to tumor cells (MDA-MB-231).

Example 4

Western Blotting Result of Anti-HLA-G Nanobody

In this example, the procedures of Western blotting for anti-HLA-G nanobody are as follows. Cells would be harvested in PRO-PREP protein extraction solution (iNtRON, Taipei, Taiwan) containing a protease inhibitor cocktail and vigorously shaken at 4° C. for 15 min, followed by centrifugation. The supernatants would be collected then the protein concentrations were determined by using the Bio-Rad BCA reagent (Bio-Rad Hercules, CA, USA). A 30 µg of each sample lysate would be subjected to electrophoresis on SDS-polyacrylamide gels then electroblotted onto PVDF membranes. After 5% BSA in TBST blocking, the membranes would be incubated with primary antibodies in TBST at 4° C. overnight. They would be then washed 4 times and incubated with horseradish peroxidase (HRP)-conjugated goat anti-mouse or rabbit IgG (Upstate, Billerica, MA, USA) for 2 hours. After washing with TBST 4 times, the blots would be incubated for 1 min with the SuperSignal West Pico ECL reagent (Pierce Biotechnology, Rockford, IL, USA), and chemiluminescence would be detected using by exposure to Kodak-X-Omat film.

Figure 3A:
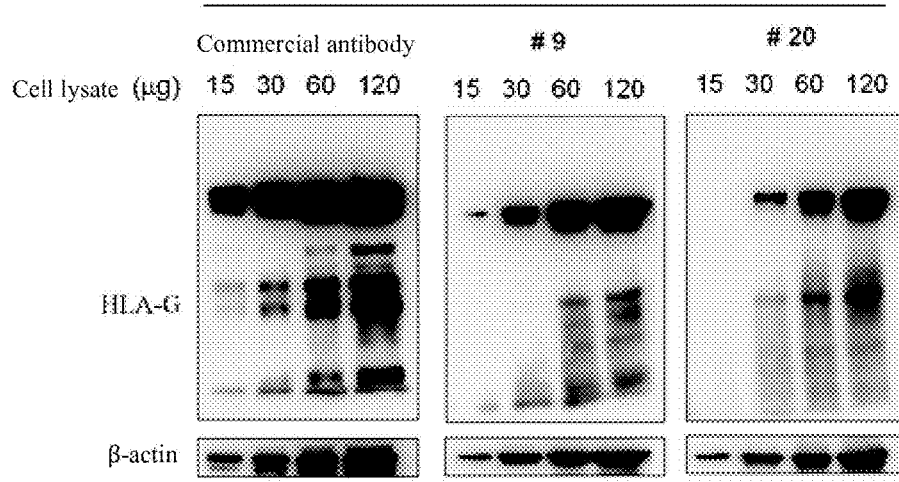
FIG. 3A shows the result of Western blotting analysis of the anti-HLA-G nanobody, the used cell line is human breast cancer cell line MDA-MB-231, the commercial antibody is HLA-G (E8N9C) XP® Rabbit mAb #79769, the number in the upper row represents the amount of cell lysate of MDA-MB-231 cell line (μg), the concentration of the primary antibody is 1 ng/ml, the secondary antibody of the commercial antibody group is anti-rabbit-horseradish peroxidase (anti-Rab-HRP)(1:1000), anti-HLA-G nanobody is heavy chain variable domain (VHH) nanobody (1 ng/ml), the secondary antibody of the experimental groups (#9 and #20) is anti-VHH-HRP (1:1000).
Figure 3B:
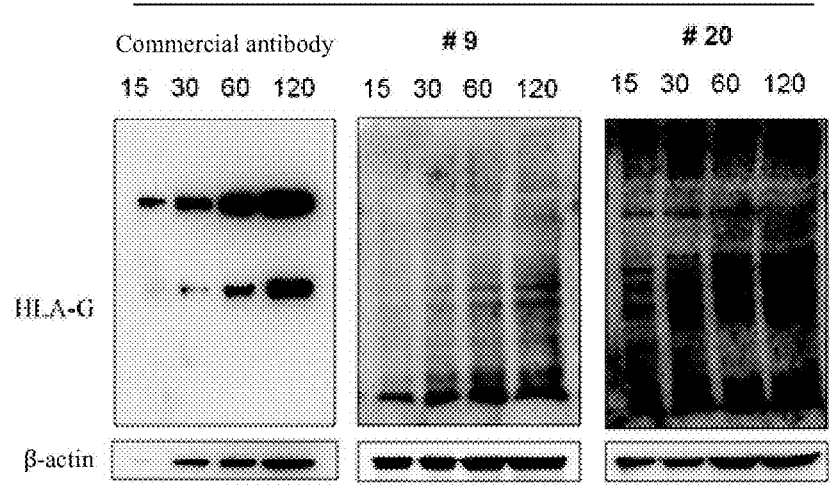
FIG. 3B shows the result of Western blotting analysis of the anti-HLA-G nanobody, the used cell line is non-small cell lung cancer cell line A549, the commercial antibody is HLA-G (E8N9C) XP® Rabbit mAb #79769, the number in the upper row represents the amount of cell lysate of A549 cell line (μ g), the concentration of the primary antibody is 1 ng/ml, the secondary antibody of the commercial antibody group is anti-rabbit-horseradish peroxidase (anti-Rab-HRP) (1:1000), anti-HLA-G nanobody is heavy chain variable domain (VHH) nanobody (1 ng/ml), the secondary antibody of the experimental groups (#9 and #20) is anti-VHH-HRP (1:1000).

The Western blotting result of anti-HLA-G nanobody is shown in FIGS. 3A and 3B, wherein the cell line used in FIG. 3A is human breast cancer cell line MDA-MB-231, the commercial antibody is HLA-G (E8N9C) XP® Rabbit mAb #79769, the number in the upper row represents the amount of cell lysate of MDA-MB-231 cell line (µg), the concentration of the primary antibody is 1 ng/ml, the secondary antibody of the commercial antibody group is anti-rabbit-horseradish peroxidase (anti-Rab-HRP)(1:1000), anti-HLA-G nanobody is heavy chain variable domain (VHH) nanobody (1 ng/ml), the secondary antibody of the experimental groups (#9 and #20) is anti-VHH-HRP (1:1000).

The cell line used in FIG. 3B is non-small cell lung cancer cell line A549 (purchased from American Type Culture Collection (ATCC)), the commercial antibody is HLA-G (E8N9C) XP Rabbit mAb #79769, the number in the upper row represents the amount of cell lysate of A549 cell line (µg), the concentration of the primary antibody is 1 ng/ml, the secondary antibody of the commercial antibody group is anti-rabbit-horseradish peroxidase (anti-Rab-HRP)(1:1000), anti-HLA-G nanobody is heavy chain variable domain (VHH) nanobody (1 ng/ml), the secondary antibody of the experimental groups (#9 and #20) is anti-VHH-HRP (1:1000). The result of this example shows that anti-HLA-G nanobodies clone #9 and #20 could recognize HLA-G protein from cellular lysate of human cancer cell line MDA-MB-231 and A549 cells by western blotting analysis.

Example 5

Flow Cytometric Analysis Result of Anti-HLA-G Nanobody

In this example, the procedures of flow cytometric analysis of anti-HLA-G nanobody are as follows. HLA-G recombinant protein (CAT #: TP305216, Origene) (0.2 mg/ml, 100 µl each well) was coated on 96-well plate overnight at 4° C. Next day, the coating buffer was discarded, and blocked with 3% skin milk for 2 hr at room temperature, followed by washing 5 times with PBST (0.05% Tween in PBS). Different concentrations of anti-HLA-G nanobody (clone #9, #20 or #33) or commercial anti-HLA-G monoclonal antibody (87G) were added overnight at 4° C. After 5 times of washing, biotinylated KIR2DL4 (Sino Biological, Cat: 13052-H02S) (0.2 mg/ml, 100 µl each well) was added for 2 hr at room temperature. After 9 times of washing, each well was incubated with 100 µl PBST containing streptavidin-HRP conjugates (ThermoFisher, Cat No: N100, dilution titer: 5000:1) for 2 hr at room temperature. After 9 times of washing with PBST, 50 µl of TMB substrate for detecting HRP activity (ThermoFisher, Cat No:N301) was added. The reactions were stopped by adding 50 µl stop solution (ThermoFisher, Cat No:N600), and it was measured by ELISA reader using 450 nm channel. The highest concentration of commercial HLA-G monoclonal antibody (87G) was set to 100% blockade of KIR2DL4/HLA-G interaction for calculating other reactions.

Figure 4:
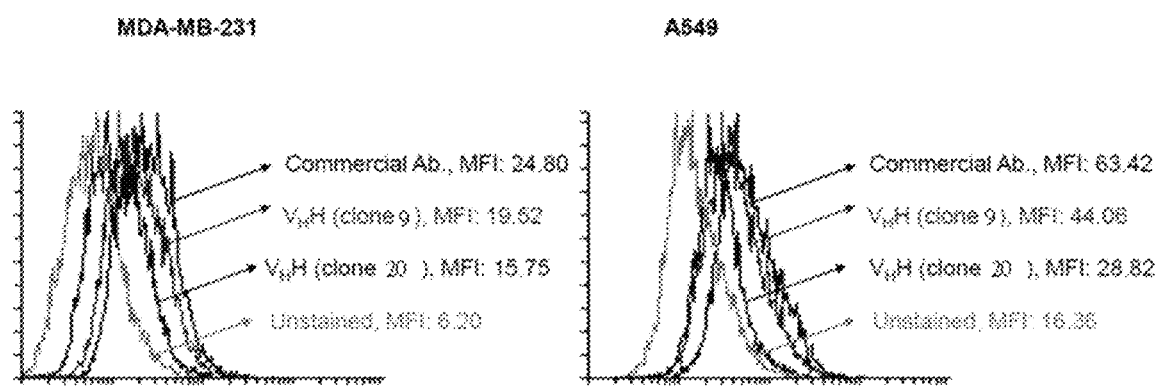
FIG. 4 shows the result of flow cytometric analysis of the anti-HLA-G nanobody, wherein the amount of human breast cancer cell line MDA-MB-231 and human non-small cell lung cancer cell line A549 is $1 \times 10^6$, the commercial antibodies (Ab) are PE (#12-9957-42) (an anti-HLA-G monoclonal antibody, 0.25 μg in 100 μl of PBS solution) and 87G, the anti-HLA-G nanobody is heavy chain variable domain (VHH) nanobody (0.25 μg in 100 μl of PBS solution), the secondary antibody is rabbit anti-camelid VHH, iFluor555 (0.5 μg in 100 μl of PBS solution), MFI represents mean fluorescence intensity.

The flow cytometric analysis result of anti-HLA-G nanobody is shown in FIG. 4, wherein the amount of human breast cancer cell line MDA-MB-231 and human non-small cell lung cancer cell line A549 is $1 \times 10^6$, the commercial antibodies (Ab) are PE (#12-9957-42) (an anti-HLA-G monoclonal antibody, 0.25 µg in 100 of PBS solution) and 87G, the anti-HLA-G nanobody is heavy chain variable domain (VHH) nanobody (0.25 µg in 100 µl of PBS solution), the secondary antibody is rabbit anti-camelid VHH, iFluor555 (0.5 µg in 100 µl of PBS solution), MFI represents mean fluorescence intensity.

Example 6

Immunocytochemistry Result of Anti-HLA-G Nanobody

In this example, the procedures of immunocytochemistry of anti-HLA-G nanobody are as follows. Tumor cells ($1 \times 10^5$) were seeded on coverslips in a 6-well plate, incubated overnight. After the indicated treatments, cells were fixed in 1% paraformaldehyde, washed with PBS, permeabilized using 0.1% Triton X-100 in PBS containing 0.5% BSA for 30 min, blocked with 2% BSA, and incubated with specific antibodies in 2% BSA/PBS containing 0.05% Tween-20 (PBST). After washing, the cells were incubated with fluorescein-conjugated secondary antibodies, washed with PBST, and mounted using a water-based mounting medium containing an anti-fade agent and 4',6-diamidino-2-phenylindole (DAPI). Images were analyzed under a Leica TCS SP8× confocal microscope (Leica).

Figure 5A:
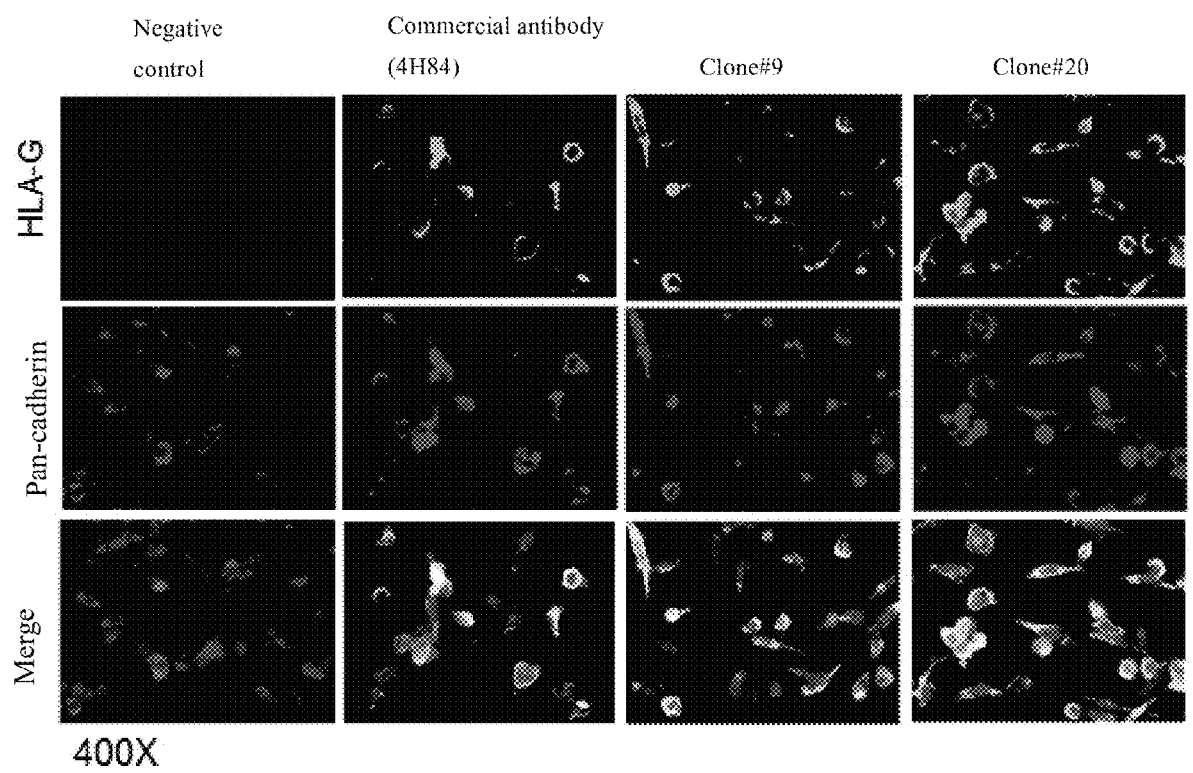
FIGS. 5A and 5B show the immunocytochemistry result of the anti-HLA-G nanobody, wherein the cell line used in FIG. 5A is human breast cancer cell line MDA-MB-231, the cell line used in FIG. 5B is human non-small cell lung cancer cell line A549, the commercial antibody 4H84 is an anti-HLA-G monoclonal antibody, the concentration of the anti-HLA-G nanobody is 1 ng/ml, and the secondary antibody is anti-VHH-fluorescein (FITC)(1:5000).
Figure 5B:
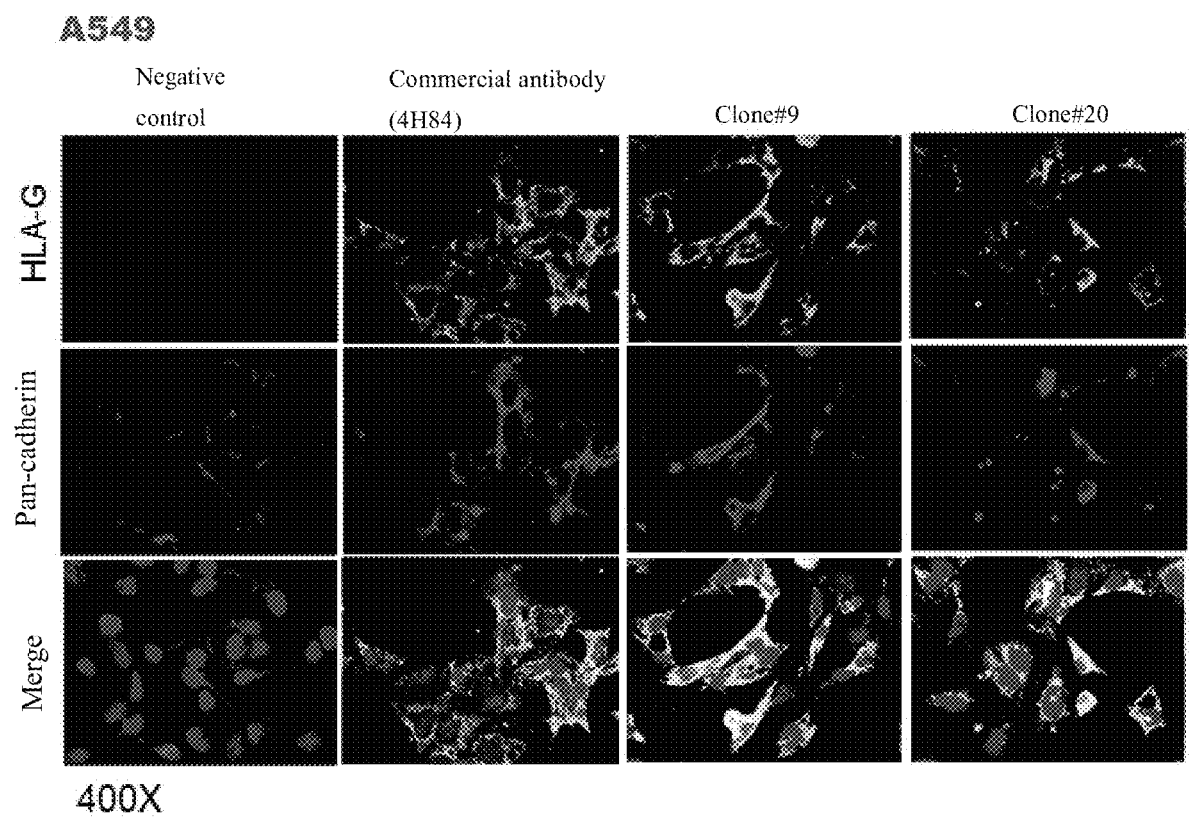

The immunocytochemistry result of anti-HLA-G nanobody is shown in FIGS. 5A and 5B, wherein the cell line used in FIG. 5A is human breast cancer cell line MDA-MB-231, the cell line used in FIG. 5B is human non-small cell lung cancer cell line A549, the commercial antibody 4H84 is an anti-HLA-G monoclonal antibody, the concentration of the anti-HLA-G nanobody is 1 ng/ml, and the secondary antibody is anti-VHH-fluorescein (FITC)(1:5000). As shown in FIGS. 5A and 5B, anti-HLA-G nanobodies clone #9 and #20 could recognize HLA-G protein on cell membrane, the expression of HLA-G was co-localized with the plasma membrane marker Pan-cadherin on MDA-MB-231 and A549 cells by immunocytochemistry using anti-HLA-G nanobodies clone #9 and clone #20, HLA-G commercial antibody 4H84 and commercial pan-cadherin antibody.

Example 7

Immunohistochemistry (IHC) Staining Result of Anti-HLA-G Nanobody

In this example, the procedures of IHC staining of anti-HLA-G nanobody are as follows. The human planceta samples would be fixed in 10% formaldehyde and embedded in paraffin. Sections (thickness=3 µm) would be processed with antigen retrieval performed microwaving at 99° C., then the sections would be washed and incubated with $H_2O_2$ for 20 min to block endogenous peroxidases, after then soaking in 5% BSA for 30 min for blocking. The primary antibodies would be incubated overnight at 4° C. After washing, the sections would be then incubated with diluted biotin-conjugated secondary antibodies for 2 h at room temperature or overnight at 4° C. Finally, the sections would be then incubated with polymer for 10 min at room temperature and following diaminobenzidine (DAB, the most sensitive and commonly used chromogenic reactant for horseradish peroxidase) staining, after then the sections would be stained lightly with hematoxylin and eosin and fixed using neutral balata. Quantification of the staining would be performed independently by optical microscope (Nikon) at 40× and 400× magnification.

Figure 6:
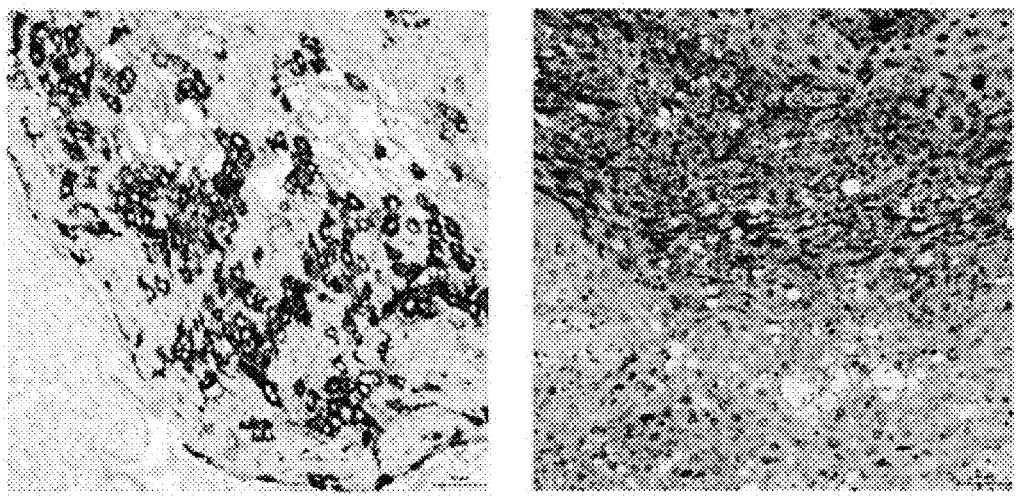
FIG. 6 shows the immunohistochemistry (IHC) staining result of the anti-HLA-G nanobody, wherein the used sample is human placenta, the commercial antibody is 4H84 (an anti-HLA-G monoclonal antibody)(#sc-21799), concentration is 200 μg/ml, working concentration is 4 μg/ml, the secondary antibody of the commercial antibody group is goat anti-rabbit HRP, DAB represents diaminobenzidine (the most sensitive and commonly used chromogenic reactant for horseradish peroxidase), the anti-HLA-G nanobody is heavy chain variable domain (VHH) nanobody (working concentration of 4 μg/ml), the antibodies of the experimental group (#9) include rabbit anti-camelid VHH antibody, biotin (0.5 μg in 100 μl of PBS solution) and goat anti-rabbit HRP.

The result of IHC staining of anti-HLA-G nanobody is shown in FIG. 6, the sample is human placenta, the commercial antibody is 4H84 (an anti-HLA-G monoclonal antibody)(#sc-21799), concentration is 200 µg/ml, working concentration is 4 μg/ml, the secondary antibody of the commercial antibody group is goat anti-rabbit HRP, DAB represents diaminobenzidine (the most sensitive and commonly used chromogenic reactant for horseradish peroxidase), the anti-HLA-G nanobody is heavy chain variable domain (VHH) nanobody (working concentration of 4 μg/ml), the antibodies of the experimental group (#9) include rabbit anti-camelid VHH antibody, biotin (0.5 μg in 100 μl of PBS solution) and goat anti-rabbit HRP. The result of this example demonstrates that anti-tumor antigen nanobody (i.e., anti-HLA-G nanobody) can be used to detect the expression of HLA-G by IHC staining.

In summary, the anti-tumor antigen nanobody (i.e., anti-HLA-G nanobody) of the present invention blocks the interaction between HLA-G and one of its receptor killer cell immunoglobulin like receptor, two Ig domains and long cytoplasmic tail 4 (KIR2DL4) and leukocyte immunoglobulin-like receptor subfamily B member 1 (LILRB1) within the 50% blocking activity as IC50 by competitive enzyme linked immunosorbent assay (ELISA), enhances cytolysis and cytotoxicity of human breast cancer cell line MDA-MB-231 with natural killer cells (NK cells), could recognize HLA-G protein from cellular lysate of human cancer cell line MDA-MB-231 and A549 cells by Western blotting analysis, and is used for flow cytometric analysis. The anti-HLA-G nanobody also could recognize HLA-G protein on cell membrane, the expression of HLA-G is co-localized with the plasma membrane marker pan-cadherin on MDA-MB-231 and A549 cells by immunocytochemistry, and is used to detect the expression of HLA-G by immunohistochemistry (IHC) staining, thereby achieving the effect of treating cancer and immune-related disorders. In particular, compared with the conventional antibodies, which have the disadvantages of low yield and poor effect, the gene must be transfected into cells by a vector to express the antibody function, the anti-tumor antigen nanobody of the present invention can be prepared in vitro on a large scale, and directly administered to the individual in need for treatment. In addition, the present invention can also achieve the effect of detecting the expression level of HLA-G.

Although the present invention has been described with reference to the preferred embodiments, it will be apparent to those skilled in the art that a variety of modifications and changes in form and detail may be made without departing from the scope of the present invention defined by the appended claims.

What is claimed is:

1. An anti-HLA-G nanobody that specifically binds to a human leukocyte antigen-G (HLA-G), wherein the anti-HLA-G nanobody consists of the amino acid sequences of SEQ ID NO: 1, SEQ ID NO: 2, or SEQ ID NO: 3, wherein the amino acid sequence of SEQ ID NOs: 1, 2, and 3 are a heavy chain variable domain (VHH) of the anti-HLA-G nanobody, wherein the anti-HLA-G nanobody is separated and purified by gel filtration chromatography.

2. The anti-HLA-G nanobody according to claim 1, which is conjugated with a fragment crystallizable region (Fc region).

3. The anti-HLA-G nanobody according to claim 2, which is conjugated with a second antibody to form a bispecific T-cell engager (BiTE), triple specific T-cell engager (TriTE), bispecific killer cell engager (BiKE), triple specific killer cell engager (TriKE), or any bispecific antibody.

4. The anti-HLA-G nanobody according to claim 3, which blocks interaction and/or binding of the HLA-G with a receptor of the HLA-G.

5. The anti-HLA-G nanobody according to claim 4, wherein the receptor is killer cell immunoglobulin like receptor, two Ig domains and leukocyte immunoglobulin-like receptor subfamily B member 1 (LILRB1).

6. An isolated nucleic acid encoding the anti-HLA-G nanobody according to claim 1, wherein the isolated nucleic acid comprises the nucleotide sequence selected from the group consisting of: SEQ ID NO: 4, SEQ ID NO: 5, SEQ ID NO:6, and any combination thereof.

7. The isolated nucleic acid according to claim 6, wherein the anti-HLA-G nanobody is conjugated with a fragment crystallizable region (Fc region).

8. The isolated nucleic acid according to claim 7, wherein the anti-HLA-G nanobody is conjugated with a second antibody to form a bispecific T-cell engager (BiTE), triple specific T-cell engager (TriTE), bispecific killer cell engager (BiKE), triple specific killer cell engager (TriKE), or any bispecific antibody.

9. The isolated nucleic acid according to claim 8, wherein the anti-HLA-G nanobody blocks interaction and/or binding of the HLA-G with a receptor of the HLA-G.

10. The isolated nucleic acid according to claim 9, wherein the receptor is killer cell immunoglobulin like receptor, two Ig domains and long cytoplasmic tail 4 (KIR2DL4) or leukocyte immunoglobulin-like receptor subfamily B member 1 (LILRB1).

11. A pharmaceutical composition, comprising the anti-HLA-G nanobody according to claim 1 and a pharmaceutically acceptable carrier.

12. The pharmaceutical composition according to claim 11, wherein the anti-HLA-G nanobody is conjugated with a fragment crystallizable region (Fc region).

13. The pharmaceutical composition according to claim 12, wherein the anti-tumor antigen nanobody is conjugated with a second antibody to form a bispecific T-cell engager (BiTE), triple specific T-cell engager (TriTE), bispecific killer cell enager (BiKE), triple specific killer cell engager (TriKE), or—any bispecific antibody.

14. The pharmaceutical composition according to claim 11, wherein the anti-HLA-G nanobody blocks interaction and/or binding of the HLA-G with a receptor of the HLA-G.

15. The pharmaceutical composition according to claim 14, wherein the receptor is killer cell immunoglobulin like receptor, two Ig domains and leukocyte immunoglobulin-like receptor subfamily B member 1 (LILRB1).

16. A method for detecting expression levels of HLA-G, comprising administering to a biological sample the anti-HLA-G nanobody according to claim 1.

17. The method according to claim 16, wherein the biological sample is blood, urine, sputum, saliva, body fluid or human placenta.

* * * * *

SEQUENCE LISTING

```
<160> NUMBER OF SEQ ID NOS: 15

<210> SEQ ID NO 1
<211> LENGTH: 133
<212> TYPE: PRT
<213> ORGANISM: Artificial Sequence
<220> FEATURE:
<223> OTHER INFORMATION: anti-HLA-G nanobody clone#9

<400> SEQUENCE: 1

Met Gly Gln Val Gln Leu Val Glu Ser Gly Gly Ser Val Gln Ala
1               5                   10                  15

Gly Gly Ser Leu Arg Leu Ser Cys Glu Ala Ser Gly Arg Thr Tyr Ser
            20                  25                  30

Ser Asn Cys Met Gly Trp Phe Arg Gln Ala Pro Gly Lys Glu Arg Glu
        35                  40                  45

Asn Val Ala Ala Ile Tyr Thr Gly Gly Asp Gly Ile Thr Tyr Ala Asp
    50                  55                  60

Ser Val Lys Gly Arg Phe Thr Ile Ser Gln Asp Lys Leu Lys Asn Met
65                  70                  75                  80

Leu Tyr Leu Gln Met Asp Ser Leu Lys Pro Glu Asp Thr Ala Met Tyr
                85                  90                  95

Tyr Cys Ala Ala Asp Pro Asn Arg Arg Arg Met Gly Val Gly Gly Ser
            100                 105                 110

Cys Leu Arg Ala Asn Phe Gly Pro Gly Gly Gln Gly Thr Gln Val Thr
        115                 120                 125

Val Ser Ser Leu Glu
    130

<210> SEQ ID NO 2
<211> LENGTH: 117
<212> TYPE: PRT
<213> ORGANISM: Artificial Sequence
<220> FEATURE:
<223> OTHER INFORMATION: anti-HLA-G nanobody clone#20

<400> SEQUENCE: 2
```

Glu Val Gln Leu Val Glu Ser Gly Gly Gly Ser Val Arg Pro Gly Glu
1               5                   10                  15

Thr Leu Arg Leu Ser Cys Thr Ala Ser Gly Phe Thr Val Asp Asp Ser
            20                  25                  30

Asp Met Ser Trp Tyr Arg Gln Ala Pro Gly Asp Glu Cys Glu Leu Val
        35                  40                  45

Ser Ser Ile Thr Ser Gly Gly Lys Tyr Tyr Ser His Pro Val Lys
    50                  55                  60

Gly Arg Phe Thr Ile Phe Arg Asp Lys Gly Lys Asn Thr Met Tyr Leu
65                  70                  75                  80

Gln Met Asn Ser Leu Val Pro Glu Asp Thr Gly Val Tyr Tyr Cys Val
            85                  90                  95

Ala Pro Ala Trp Thr Gly Tyr Gly Cys Thr Trp Gly Gln Gly Thr Gln
        100                 105                 110

Val Thr Val Ser Ser
        115

<210> SEQ ID NO 3
<211> LENGTH: 132
<212> TYPE: PRT
<213> ORGANISM: Artificial Sequence
<220> FEATURE:
<223> OTHER INFORMATION: anti-HLA-G nanobody clone#33

<400> SEQUENCE: 3

Met Gly His Val Gln Leu Val Glu Ser Gly Gly Gly Ser Val Gln Ala
1               5                   10                  15

Gly Gly Ser Leu Lys Leu Ser Cys Val Thr Ser Ala Tyr Thr Phe Ser
            20                  25                  30

Ala Ser Gly Asn Cys Met Gly Trp Leu Arg Gln Ala Pro Gly Lys Gly
        35                  40                  45

Arg Glu Gly Ile Ala Ala Thr Tyr Thr Arg Ser Ala Lys Thr Tyr Tyr
    50                  55                  60

Ala Asp Ser Val Lys Gly Arg Phe Thr Ile Ser Gln Asp Asn Ala Lys
65                  70                  75                  80

Asn Thr Val Tyr Leu Gln Met Asn Gly Leu Lys Pro Glu Asp Thr Ala
            85                  90                  95

Thr Tyr Tyr Cys Ala Val Ala Arg Cys Ala Gly Arg Pro Asp Arg Ser
        100                 105                 110

Thr Leu Thr Ser Phe Ala Trp Trp Gly Gln Gly Thr Gln Val Thr Val
        115                 120                 125

Ser Ser Leu Glu
    130

<210> SEQ ID NO 4
<211> LENGTH: 399
<212> TYPE: DNA
<213> ORGANISM: Artificial Sequence
<220> FEATURE:
<223> OTHER INFORMATION: anti-HLA-G nanobody clone#9

<400> SEQUENCE: 4
atgggccagg tgcagctggt ggaaagcggc ggcggtagtg ttcaggcagg tggcagcctg      60
cgcctgagtt gtgaagcaag cggccgcacc tatagcagca attgcatggg ttggtttcgc     120
caggcaccgg gcaagaaacg cgaaaatgtg gcagcaatct ataccggcgg tgacggtatt     180
acctatgccg atagtgtgaa aggtcgtttt accattagtc aggataaact gaaaaacatg     240

```
ctgtatctgc agatggatag cctgaaaccg aagataccg ccatgtatta ttgcgcagca    300
gatccgaatc gccgccgtat gggcgttggt ggcagctgcc tgcgcgccaa ttttggcccg    360
ggcggccagg gtacccaggt gaccgttagc agcctcgag                          399
```

<210> SEQ ID NO 5
<211> LENGTH: 351
<212> TYPE: DNA
<213> ORGANISM: Artificial Sequence
<220> FEATURE:
<223> OTHER INFORMATION: anti-HLA-G nanobody clone#20

<400> SEQUENCE: 5

```
gaagtgcagc tggttgaaag tggtggtggc agcgttcgcc cgggcgaaac cttacgtctg     60
agctgcaccg caagtggctt caccgtggat gatagcgata tgagctggta tcgccaggcc    120
ccgggtgatg aatgtgaact ggttagtagc attaccagtg gtggcggcaa atattatagt    180
catccggtga aaggccgctt caccatcttc cgtgataaag gtaaaaatac catgtatctg    240
cagatgaata gcctggttcc ggaagatacc ggcgtgtatt attgtgtggc cccggcctgg    300
accggctatg gttgcacctg gggccagggt acccaggtga ccgttagcag t             351
```

<210> SEQ ID NO 6
<211> LENGTH: 396
<212> TYPE: DNA
<213> ORGANISM: Artificial Sequence
<220> FEATURE:
<223> OTHER INFORMATION: anti-HLA-G nanobody clone#33

<400> SEQUENCE: 6

```
atgggccatg ttcagctggt tgaaagtggc ggtggcagtg tgcaggccgg tggtagtctg     60
aaactgagct gcgttaccag cgcatatacc ttcagcgcaa gcggtaattg tatgggctgg    120
ctgcgtcagg caccgggtaa aggccgcgaa ggtattgcag ccacctatac cgtagtgcc     180 aaaacctatt atgcagatag tgttaaaggt cgcttcacca ttagtcagga taatgcaaaa    240
aataccgtgt atctgcagat gaatggtctg aaaccggaag ataccgccac ctattattgt    300
gcagtggcac gctgtgccgg tcgtccggat cgtagtaccc tgaccagctt cgcctggtgg    360
ggtcagggca cccaggtgac cgtgagcagc ctcgag                              396
```

<210> SEQ ID NO 7
<211> LENGTH: 8
<212> TYPE: PRT
<213> ORGANISM: Artificial Sequence
<220> FEATURE:
<223> OTHER INFORMATION: CDR1 of anti-HLA-G nanobody clone#9

<400> SEQUENCE: 7

```
Gly Arg Thr Tyr Ser Ser Asn Cys
1               5
```

<210> SEQ ID NO 8
<211> LENGTH: 8
<212> TYPE: PRT
<213> ORGANISM: Artificial Sequence
<220> FEATURE:
<223> OTHER INFORMATION: CDR2 of anti-HLA-G nanobody clone#9

<400> SEQUENCE: 8

```
Ile Tyr Thr Gly Gly Asp Gly Ile
1               5
```

```
<210> SEQ ID NO 9
<211> LENGTH: 15
<212> TYPE: PRT
<213> ORGANISM: Artificial Sequence
<220> FEATURE:
<223> OTHER INFORMATION: CDR3 of anti-HLA-G nanobody clone#9

<400> SEQUENCE: 9

Ala Ala Asp Pro Asn Arg Arg Arg Met Gly Val Gly Gly Ser Cys
1               5                   10                  15

<210> SEQ ID NO 10
<211> LENGTH: 8
<212> TYPE: PRT
<213> ORGANISM: Artificial Sequence
<220> FEATURE:
<223> OTHER INFORMATION: CDR1 of anti-HLA-G nanobody clone#20

<400> SEQUENCE: 10

Gly Phe Thr Val Asp Asp Ser Asp
1               5

<210> SEQ ID NO 11
<211> LENGTH: 7
<212> TYPE: PRT
<213> ORGANISM: Artificial Sequence
<220> FEATURE:
<223> OTHER INFORMATION: CDR2 of anti-HLA-G nanobody clone#20

<400> SEQUENCE: 11

Ile Thr Ser Gly Gly Gly Lys
1               5

<210> SEQ ID NO 12
<211> LENGTH: 11
<212> TYPE: PRT
<213> ORGANISM: Artificial Sequence
<220> FEATURE:
<223> OTHER INFORMATION: CDR3 of anti-HLA-G nanobody clone#20

<400> SEQUENCE: 12

Val Ala Pro Ala Trp Thr Gly Tyr Gly Cys Thr
1               5                   10

<210> SEQ ID NO 13
<211> LENGTH: 8
<212> TYPE: PRT
<213> ORGANISM: Artificial Sequence
<220> FEATURE:
<223> OTHER INFORMATION: CDR1 of anti-HLA-G nanobody clone#33

<400> SEQUENCE: 13

Ala Tyr Thr Phe Ser Ala Ser Gly
1               5

<210> SEQ ID NO 14
<211> LENGTH: 10
<212> TYPE: PRT
<213> ORGANISM: Artificial Sequence
<220> FEATURE:
<223> OTHER INFORMATION: CDR2 of anti-HLA-G nanobody clone#33

<400> SEQUENCE: 14

Ala Ala Thr Tyr Thr Arg Ser Ala Lys Thr
1               5                   10

<210> SEQ ID NO 15
```

```
<211> LENGTH: 19
<212> TYPE: PRT
<213> ORGANISM: Artificial Sequence
<220> FEATURE:
<223> OTHER INFORMATION: CDR3 of anti-HLA-G nanobody clone#33

<400> SEQUENCE: 15

Ala Val Ala Arg Cys Ala Gly Arg Pro Asp Arg Ser Thr Leu Thr Ser
1               5                   10                  15

Phe Ala Trp
```